(12) United States Patent
Kawakami et al.

(10) Patent No.: US 8,551,608 B2
(45) Date of Patent: Oct. 8, 2013

(54) COMPOSITE SHEET AND ABSORBENT ARTICLE USING COMPOSITE SHEET

(75) Inventors: Yusuke Kawakami, Kagawa (JP); Kozo Abe, Kagawa (JP); Minako Sagisaka, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 451 days.

(21) Appl. No.: 12/593,425

(22) PCT Filed: Mar. 21, 2008

(86) PCT No.: PCT/JP2008/055326
§ 371 (c)(1),
(2), (4) Date: Nov. 4, 2010

(87) PCT Pub. No.: WO2008/123157
PCT Pub. Date: Oct. 16, 2008

(65) Prior Publication Data
US 2011/0046586 A1   Feb. 24, 2011

(30) Foreign Application Priority Data
Mar. 30, 2007   (JP) ................................. 2007-094457

(51) Int. Cl.
*A61F 13/15*   (2006.01)
*D04H 13/00*   (2006.01)

(52) U.S. Cl.
USPC ........................... 428/220; 604/358; 442/328

(58) Field of Classification Search
USPC .................... 604/358; 442/328; 428/220
See application file for complete search history.

(56) References Cited

U.S. PATENT DOCUMENTS

| | | | |
|---|---|---|---|
| 3,616,157 A * | 10/1971 | Smith | 428/171 |
| 4,657,802 A | 4/1987 | Morman | |
| 4,720,415 A * | 1/1988 | Vander Wielen et al. | 428/152 |
| 4,781,966 A | 11/1988 | Taylor | |
| 6,733,482 B1 | 5/2004 | Coles et al. | |
| 2005/0148263 A1 | 7/2005 | Zhou et al. | |

(Continued)

FOREIGN PATENT DOCUMENTS

CN   1742128 A   3/2006
EP   1 589 140 A1   10/2005

(Continued)

OTHER PUBLICATIONS

International Search Report from corresponding PCT application No. PCT/JP2008/055326, dated Jun. 17, 2008, 4 pages.

(Continued)

*Primary Examiner* — David Sample
*Assistant Examiner* — Tahseen N Khan
(74) *Attorney, Agent, or Firm* — Brinks Hofer Gilson & Lione

(57) ABSTRACT

It is intended to provide a composite sheet which is excellent in comfort to the skin face when used in an absorbent article such as a disposable diaper. A composite sheet (1) fabricated by bonding stretchable nonwoven fabric (2) to a non-stretchable sheet (3) using an adhesive (4). The stretchable nonwoven fabric (2) is bonded in the stretched state to the non-stretchable sheet. The composite sheet (1) has a contact area ratio of 65% or more and an air permeation resistance of 0.20 KPa·s/m or less. By satisfying these numerical requirements, the composite sheet shows excellent sweat absorption properties and air permeability when used as a constituting member of an absorbent article such as a disposable diaper.

8 Claims, 10 Drawing Sheets

(56) References Cited

U.S. PATENT DOCUMENTS

| | | |
|---|---|---|
| 2005/0245162 A1 | 11/2005 | McCormack et al. |
| 2006/0121812 A1* | 6/2006 | Suzuki et al. ............... 442/411 |
| 2006/0135024 A1 | 6/2006 | Thomas et al. |
| 2006/0141883 A1 | 6/2006 | Nishiguchi et al. |
| 2009/0275909 A1* | 11/2009 | Sakaguchi ............... 604/385.23 |

FOREIGN PATENT DOCUMENTS

| | | |
|---|---|---|
| EP | 2 087 867 A1 | 8/2009 |
| EP | 2 090 424 A1 | 8/2009 |
| EP | 2 095 939 A1 | 9/2009 |
| JP | 09-078431 | 3/1997 |
| JP | 2000-189454 | 7/2000 |
| JP | 2003-153955 | 5/2003 |
| JP | 2003-187051 | 7/2003 |
| JP | 2003-299689 | 10/2003 |
| JP | 2004-113602 | 4/2004 |
| JP | 2004-174209 | 6/2004 |
| JP | 2004-244791 | 9/2004 |
| JP | 2004-248853 | 9/2004 |
| JP | 2005-124594 | 5/2005 |
| JP | 2005-296326 | 10/2005 |
| JP | 2005-304899 | 11/2005 |
| JP | 2006-045291 | 2/2006 |
| JP | 2007-528760 | 10/2007 |
| JP | 2008-246995 | 10/2008 |
| TW | 418085 | 1/2001 |
| TW | 200603989 A | 2/2006 |
| WO | WO2006/087166 A1 | 9/2005 |
| WO | WO 2006/017518 A2 | 2/2006 |
| WO | WO 2008004456 A1 * | 1/2008 |

OTHER PUBLICATIONS

Extended Supplementary European Search Report based on corresponding European Application No. 08738719.7, dated Dec. 8, 2011 (9 pgs).

Taiwanese Office Action based on corresponding Taiwanese Application No. 097111475, mailed May 31, 2013 (12 pgs).

* cited by examiner

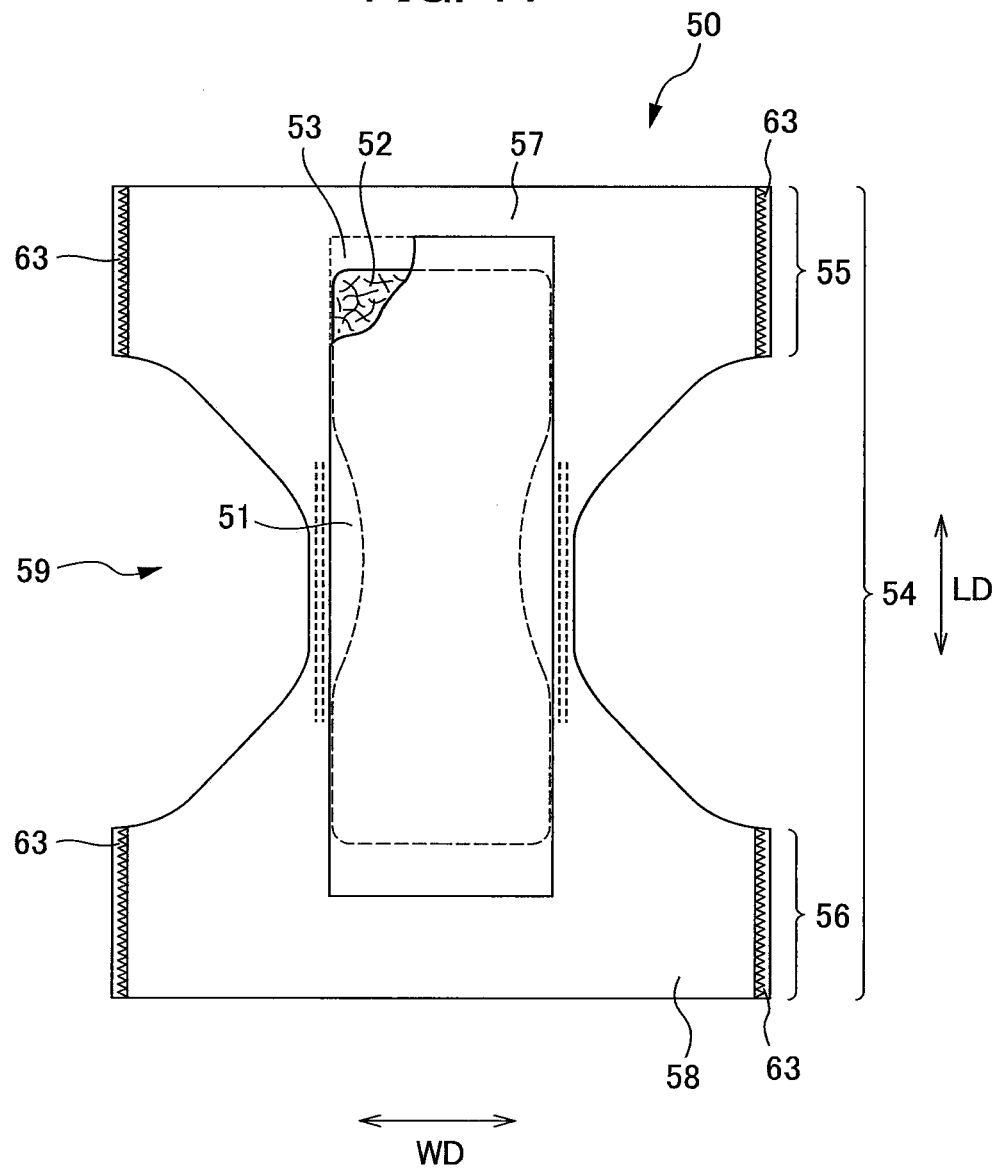

COMPOSITE SHEET AND ABSORBENT ARTICLE USING COMPOSITE SHEET

RELATED APPLICATIONS

The present application is a 35 U.S.C. §371 national stage filing of International Patent Application No. PCT/JP2008/055326, filed Mar. 21,2008, to which priority is claimed under 35 U.S.C. §120 and through which priority is claimed under 35 U.S.C. §119 to Japanese Priority Patent Application No. 2007-094457, filed Mar. 30,2007.

TECHNICAL FIELD

The present invention relates to a composite sheet and an absorbent article using the composite sheet.

BACKGROUND ART

An absorbent article such as a disposable diaper is required to stretch, so as to suit the movement of the body of a wearer without causing the wearer to feel uncomfortable. To satisfy this requirement, the absorbent article has been made of various components obtained by combining a nonwoven fabric and an elastic member.

Accordingly, these constituent members have been attempted numerous improvements for the purpose of improving the comfort of the absorbent article worn by the wearer, for example, improvements in breathability and sweat absorbability.

For example, Japanese Laid-Open Publication No. 2000-189454 (hereinafter referred to as Patent Document 1) shown below discloses a disposable diaper designed for the purpose of improving the breathability and sweat absorbability of the disposable diaper by an end flap formed in a waist band area that is breathable, and a breathable sweat-absorbent sheet on an inner face thereof.

DISCLOSURE OF THE INVENTION

Problems to be Solved by the Invention

Patent Document 1 discloses that an end flap having a breathable sweat-absorbent sheet is attached with a linear elastic member that elastically stretches in the direction of the waist. This elastic member stretches linearly only in the direction of the waist. Thus, the breathable sweat-absorbent sheet also irregularly compresses in accordance with the stretched elastic member, thereby causing a contact area between the sheet and skin to be reduced. Accordingly, heat or sweat is trapped between breathable sweat-absorbent sheet and skin, causing discomfort when the diaper is being worn. Furthermore, the linear elastic member also causes local linear pressure, increasing physical irritation towards the skin, which causes the wearer to feel uncomfortable.

As described above, in order to maintain the comfort of the wearer of the disposable diaper, the following two factors must be satisfied: 1) physical irritation to the skin must be reduced, and 2) to maintain the appropriate degree of skin moisture (to appropriately ensure sweat absorbability and breathability). However, factor 2) has been particularly difficult to achieve in the conventional constituent members.

Accordingly, an objective of the present invention is to provide a composite sheet that prevents heat and sweat from accumulating therein, and that also can reduce physical irritation to the skin, to thereby provide comfort to the skin surface of the wearer when being used in an absorbent article such as a disposable diaper.

Means for Solving the Problems

The present inventors have focused on an elastic composite sheet, in which a nonwoven fabric in an elongated state is partially joined to a non-elastic sheet. Accordingly, in this present configuration, the present inventors also have newly discovered that the comfort felt by the wearer with regard to the skin surface is related to the contact area ratio with regard to the skin and the breathability of the composite sheet, and that such a configuration can be adjusted to also eliminate the so-called sticky feeling, without the accumulation heat and sweat at the time of wear. Specifically, the present inventors have discovered that the composite sheet having a contact area ratio and a breathability within a predetermined range can achieve the abovementioned 2) to maintain the appropriate degree of skin moisture (to appropriately ensure sweat absorbability and breathability).

According to the present invention, the superior elasticity exhibited by the entire composite sheet may allow the composite sheet to function when needed, as a constituent member of the disposable diaper, including a waist gather section, even without using the elastic member. Thus, the abovementioned 1), by which physical irritation to the skin is reduced, can also be achieved when needed.

Specifically, the present invention provides the following:

In a first aspect of the present invention, a composite sheet consists of an elastic nonwoven fabric in an elongated state is bonded to a non-elastic sheet, in which any one surface of the composite sheet has a contact area ratio of at least 65% at a time of 135% elongation and at a time of 170% elongation, and the composite sheet has a airflow resistance value of no more than 0.20 KPa·s/m at a time of 150% elongation (in which the contact area ratio is an area percentage of water-based paint transferred to filter paper after being applied onto one surface of the composite sheet in the elongated state, with the filter paper superimposing the water-based paint being retained thereon for 10 seconds under 250 g of weight).

In a second aspect of the composite sheet as described in a first aspect of the present invention, the elastic nonwoven fabric has a plurality of strip-shaped low-density regions and a plurality of strip-shaped high-density regions that are alternately and continuously formed on both sides, with the strip-shaped high-density regions on one surface and the strip-shaped high-density regions on the other surface being alternately formed.

In a third aspect of the composite sheet described in either of aspects 1 or 2 of the present invention, the non-elastic sheet is bonded to the elastic nonwoven fabric by adhesive agent.

In a fourth aspect of the composite sheet described in aspects 1 to 3, of the present invention, the composite sheet has the contact area ratio of at least 80% on a surface of the elastic nonwoven fabric.

In a fifth aspect of the composite sheet described in aspects 1 to 4 of the present invention, the composite sheet has a condensation amount of no greater than 7 g/m$^2$ at the time of 150% elongation (in which the condensation amount is the amount of water adhering to an opposing surface of the composite sheet after the composite sheet is arranged to oppose a water surface at a temperature of 40 degrees C., and left for one hour under an atmosphere of 20 degrees C.×60% RH).

In a sixth aspect of the composite sheet described in aspects 1 to 5 of the present invention, the composite sheet has a transpiration rate of at least 65% in at the time of 150% elongation.

In a seventh aspect of the composite sheet described in aspects 1 to 6 of the present invention, the composite sheet has a moisture permeation level of at least 3000 g/m²·24 hours·atom at the time of 150% elongation.

In an eighth aspect of the composite sheet described in aspects 1 to 7 of the present invention, the elastic nonwoven fabric includes at least a partially-elongated thermoplastic fiber and an elastomer fiber, which is different from the thermoplastic fiber.

In a ninth aspect of the composite sheet described in aspects 1 to 8 of the present invention, the elastomer fiber and the thermoplastic fiber in the elastic nonwoven fabric are mixed at a ratio of 80:20 to 25:75.

In a tenth aspect of the composite sheet described in aspects 1 to 9 of the present invention, both surfaces of the elastic nonwoven fabric are bonded with non-elastic sheets.

In an eleventh aspect an absorbent article consists of at least an absorber and the composite sheet described in aspects 1 to 10 of the present invention, the composite sheet being disposed at a skin-abutting surface of the absorbent article when the absorbent article is being worn.

In a twelfth aspect of the absorbent article described in aspect 11 of the present invention, the absorbent article including: a substantially vertically-shaped absorber disposed along the longitudinal direction, the absorber having a longitudinal direction and a width direction perpendicular to the longitudinal direction; and a composite sheet disposed so that the width direction is the elongation direction, the composite sheet having U-shaped notches inward from the inner side formed at both edges in the width direction.

In a thirteenth aspect of the absorbent article described in aspect 12 of the present invention, a surface of the elastic nonwoven fabric is disposed at a skin-abutting surface.

In a fourteenth aspect, the composite sheet includes an elastic nonwoven fabric disposed at a skin-abutting surface when an absorbent article is worn, in which, at least one surface of the composite sheet has a contact area ratio of no less than 65% at the time of 135% elongation and at the time of 170% elongation, and the composite sheet has an airflow resistance value of at least 0.20 KPa·s/m at the time of 150% elongation (in which the contact area ratio is an area percentage of water-based paint transferred to filter paper after being applied onto one surface of the composite sheet in the elongated state, with the filter paper superimposing the water-based paint being retained thereon for 10 seconds under 250 g of weight).

Effects of the Invention

According to the present invention, in a composite sheet is provided in which an elastic nonwoven fabric in an elongated form is attached to a non-elastic sheet via the employment of a hot-melt adhesive agent, a contact area ratio and breathability thereof being in a predetermined range to prevent heat and sweat from being accumulated when a diaper is worn, and to also eliminate a so-called sticky feeling.

BRIEF DESCRIPTION OF THE DRAWINGS

FIG. 11 is a development view illustrating a disposable diaper according to the present invention.

PREFERRED MODE FOR CARRYING OUT THE INVENTION

Hereinafter, the structure of the composite sheet of the present invention will be explained, followed by the required predetermined properties thereof, and finally, an absorbent article employing such a composite sheet.

[Structure of Composite Sheet]

Figure 1:
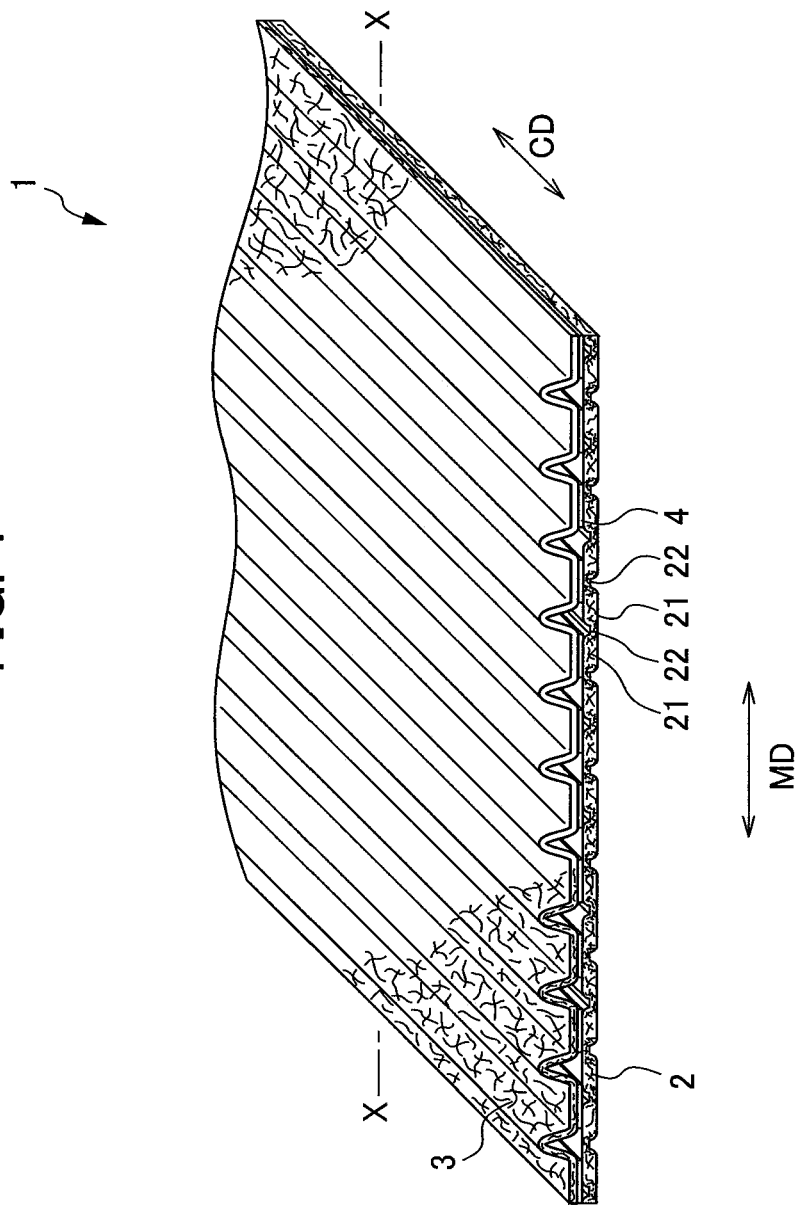
FIG. 1 is a perspective view illustrating a composite sheet according to the present invention.
Figure 2:
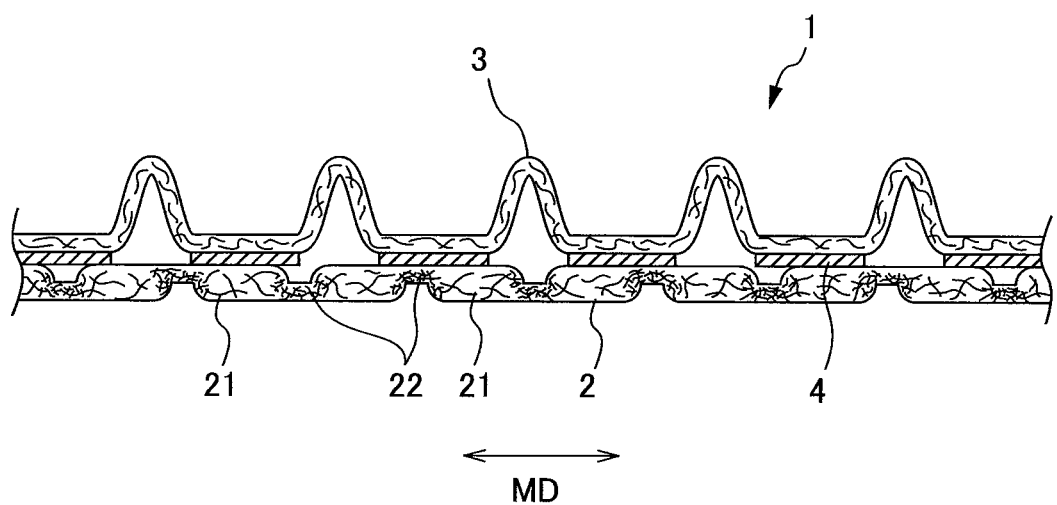
FIG. 2 is an expanded cross-sectional view taken along a direction X-X of FIG. 1.

FIG. 1 is a perspective view illustrating one embodiment of the composite sheet of the present invention. FIG. 2 is an expanded cross-sectional view taken along the direction X-X of FIG. 1. As shown in FIG. 1 and FIG. 2, a composite sheet 1 of the present invention is a sheet obtained by the adhesion of an elastic nonwoven fabric 2 to a non-elastic sheet 3 via adhesive agent 4. Specifically, the composite sheet 1 consists of the elastic nonwoven fabric 2 in an elongated state bonded to the non-elastic sheet 3 while the elastic nonwoven fabric 2.

The composite sheet 1 is formed by applying the adhesive agent 4 to the non-elastic sheet 3 in strip-shaped fixed intervals, to bond the non-elastic sheet 3 to the elongated elastic nonwoven fabric 2. Thus, when the elongated state of the elastic nonwoven fabric 2 is undone, the non-elastic sheet 3 is adhered to elastic nonwoven fabric 2 in accordance with the adhesion pattern coated thereon via the adhesive agent 4, such that the uncoated parts sag to form a plurality of wrinkles in a regular manner. Moreover, the application of the adhesive agent of the present invention is not limited to an intermittent application, as in this embodiment, may also include an entire application.

Figure 3:
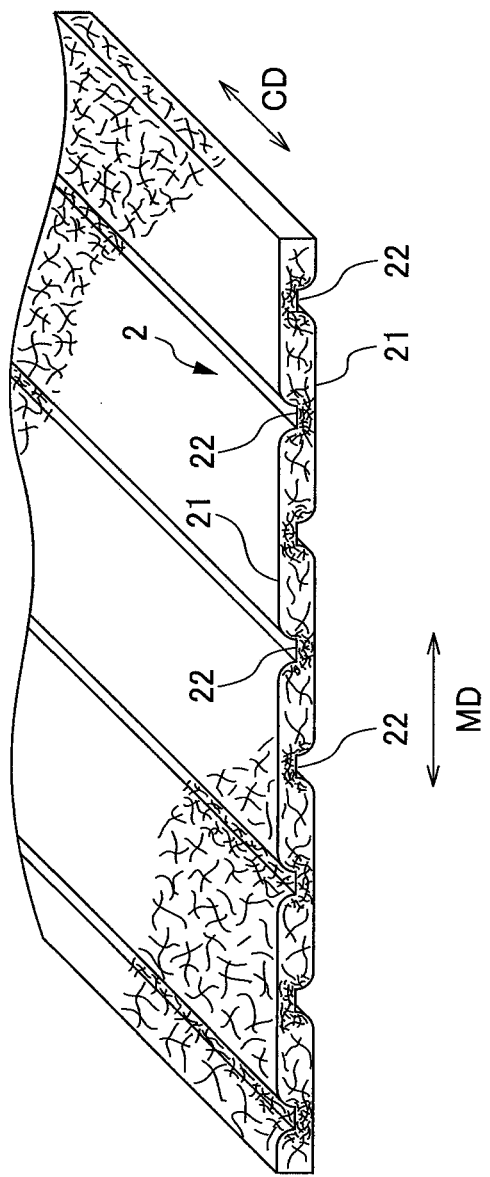
FIG. 3 is a perspective view illustrating an elastic nonwoven fabric according to the present invention.

FIG. 3 is a perspective view illustrating the elastic nonwoven fabric 2. As shown in FIG. 3, the elastic nonwoven fabric 2 is a nonwoven fabric obtained by randomly arranging and forming elastomer fibers and elastic thermoplastic fibers. The elastic nonwoven fabric 2, which is one example of the elastic nonwoven fabric of the present invention, is formed by using a gear processing (described hereinafter) to alternately form low-density regions 21 as a plurality of strip-shaped low-density regions, and high-density regions 22 as a plurality of strip-shaped high-density regions over both surfaces in a manufacturing flow direction along which a nonwoven fabric is conveyed via an apparatus for manufacturing a nonwoven fabric (Machine Direction: MD). The plurality of high-density regions 22 on one surface and the plurality of high-density regions 22 on the other surface are alternately formed in the manufacturing flow direction (MD) of the composite sheet 1.

The elastic nonwoven fabric 2 can be made of elastic thermoplastic fibers, such as polyolefin-base fiber or polyester-base fiber. Specifically, the elastic nonwoven fabric 2 can be made of polypropylene, polyethylene, polyethylene terephthalate, or polybutylene terephthalate. The elastic nonwoven fabric 2 also can be made of elastomer fibers, such as urethane-base, polystyrene-base, or rubber-base fibers. Specifically, the elastic nonwoven fabric 2 can be made of polyurethane, for example.

The elastic thermoplastic fiber may be mixed with the elastomer fiber at a mixing ratio (weight ratio) from 80:20 to 25:75. When the mixing ratio of the elastic thermoplastic fibers is greater than 80%, the distortion of the elastic nonwoven fabric 2 may be increased. On the other hand, when the mixing ratio of the elastomer fiber is greater than 75%, the elastomer fiber may feel sticky to the wearer. Moreover, the thermoplastic fiber and the elastomer fiber preferably have an average fiber diameter of 10 to 35 μm. Furthermore, the thermoplastic fiber and the elastomer fiber are randomly combined.

In addition, the strength required for the composite sheet 1 is preferably obtained from an elastic nonwoven fabric 2 having basis weight of 20 g/m$^2$ to 100 g/m$^2$ in a relaxed state. The elastic thermoplastic fiber in a relaxed state preferably has a basis weight of 4 g/m$^2$ to 60 g/m$^2$. The elastomer fiber preferably has a basis weight of 5 g/m$^2$ to 70 g/m$^2$.

Figure 4:
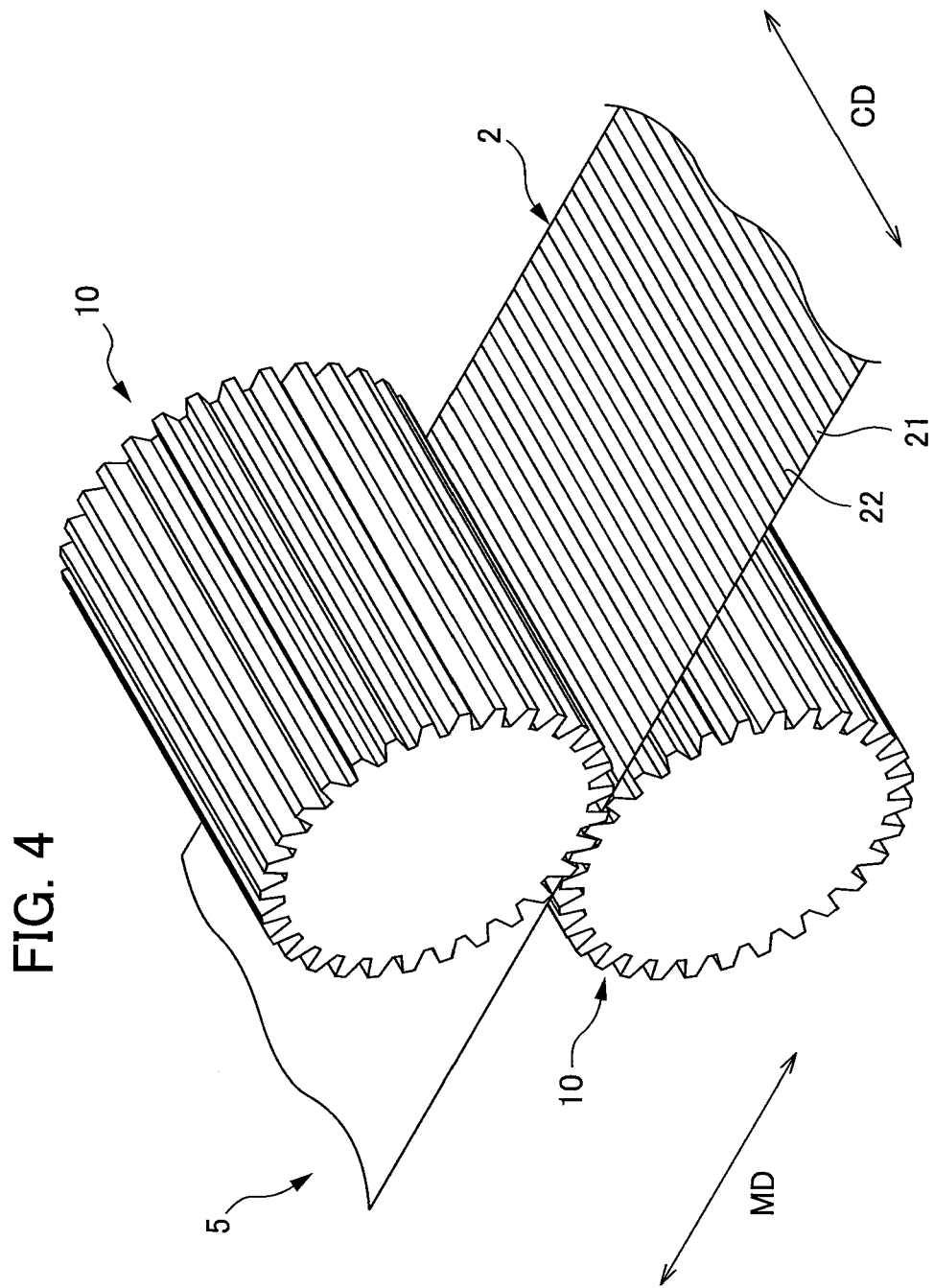
FIG. 4 is a schematic view according to the present invention illustrating being formed an elastic nonwoven fabric by gear elongation processing against a raw elastic nonwoven fabric related to the present invention.

FIG. 4 illustrates a raw elastic nonwoven fabric original fabric subjected to gear elongation processing. The raw elastic nonwoven fabric 5 is compressed via a pair of filler rolls 10 to elongate the elastic thermoplastic fiber, such that this combined with elasticity of the elastomer fiber, provides an elastic property to the raw elastic nonwoven fabric 5. However, the abovementioned elongation processing means is specifically not limited to the gear processing described above, and thus, may also be performed by another roll elongation process for example.

The non-elastic sheet 3 can be appropriately changed depending on the purpose therefore. For example, the non-elastic sheet 3 can be made of various known nonwoven fabrics, such as a spunlaid nonwoven fabric; a melt-blown nonwoven fabric; a heat rolled nonwoven fabric; an SMS nonwoven fabric combining a spunlaid nonwoven fabric with a melt-blown nonwoven fabric; an air-through nonwoven fabric; a spunlaced nonwoven fabric, or an airlaid nonwoven fabric. The non-elastic sheet 3 preferably has a basis weight of 10 g/m$^2$ to 50 g/m$^2$.

The composite sheet 1 is formed by the adhesion of the elastic nonwoven fabric 2 to the non-elastic sheet 3 via the adhesive agent 4. The adhesive agent 4 is preferably a hot-melt adhesive agent, for example. Accordingly, the composite sheet 1 is formed with the non-elastic sheet 3 being attached to the elastic nonwoven fabric 2 in an elongated state via the adhesive agent 4. An interval between adjacent hot-melt bonds is within 15 mm, and preferably within 10 mm. The adhesive agent 4 preferably has a basis weight of 0.5 g/m$^2$ to 15 g/m$^2$.

Figure 5:
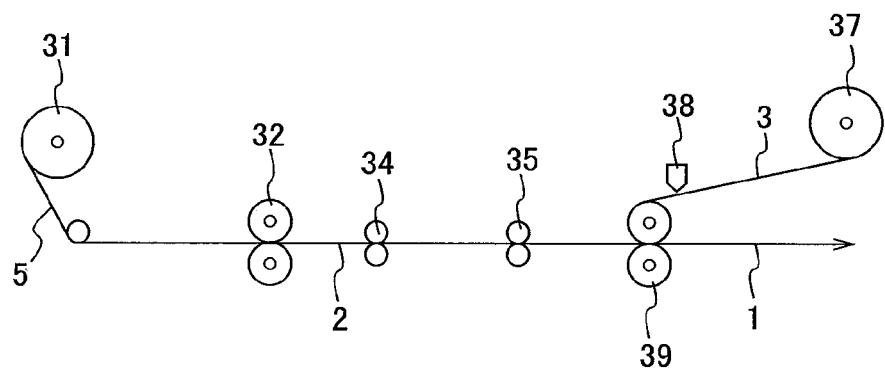
FIG. 5 describes a method for manufacturing the composite sheet according to the present invention.

FIG. 5 shows one example of the manufacturing method of the composite sheet 1. First, the pre-elongation processed raw elastic nonwoven fabric 5 wound around raw fabric roll 31 is drawn. Next, the raw elastic nonwoven fabric 5 is inserted between a pair of gear rolls 32 and subjected to the gear elongation processing. Therefore, the raw elastic nonwoven fabric 5 become an elastic nonwoven fabric 2 exhibiting elasticity. Next, elastic nonwoven fabric 2 exhibiting elasticity is elongated by using rolls 34 and 35, to subsequently being conveyed the elastic nonwoven fabric 2 between nip rolls 39. On the other hand, the non-elastic sheet 3 wound around an original fabric roll 37 is coated with a hot-melt adhesive agent at prescribed regions of the elastic sheet 3 by an adhesive agent coating apparatus 38 and conveyed between the pair of nip rolls 39. The elastic nonwoven fabric 2 and the non-elastic sheet 3 can be simultaneously conveyed between the nip rolls 39 to bond the elastic nonwoven fabric 2 to the non-elastic sheet 3. Thereafter, the elongated state of the elastic nonwoven fabric 2 and the non-elastic sheet 3 can be undone to obtain the composite sheet 1. Moreover, the composite sheet 1 obtained thereby preferably has an elongation rate of at least 150% to no greater than 350%, and a thickness of at least 1 mm to no greater than 4 mm.

Figure 6:
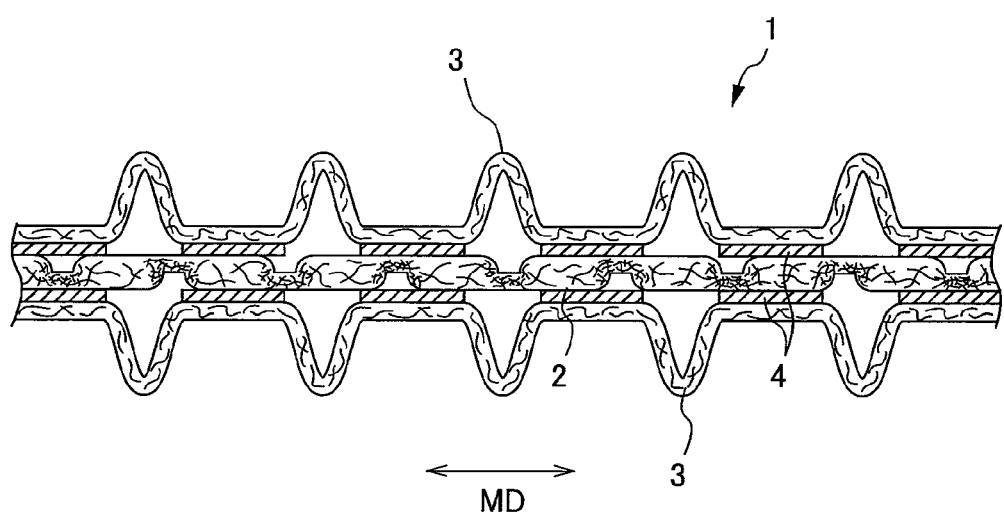
FIG. 6 is an expanded cross-sectional view illustrating another embodiment of the composite sheet according to the present invention.

Furthermore, the composite sheet of the present invention is not specifically limited to the two-layered configuration of the above described elastic nonwoven fabric 2 and the non-elastic sheet 3. For example, the composite sheet of the present invention may also have a three-layered configuration as shown in the non-elastic sheet 3, the elastic nonwoven fabric 2, and the non-elastic sheet 3 of FIG. 6.

[Properties of Composite Sheet]
Contact Area Ratio

In the present invention, at least one surface of the abovementioned composite sheet 1 has a contact area ratio is at least 65% at the time of 135% elongation and the time of 170% elongation. The abovementioned value of the contact area ratio is preferably at least 80%, and more preferably at least 90%. Moreover, the value of the contact area ratio preferably has an upper limit of no greater than 99%.

The concept of "contact area ratio" represents a parameter obtained by digitizing the contact rate to the skin when the composite sheet is employed on a skin-abutting surface. Accordingly, it was discovered that one of characteristic of the present invention is that, the higher the value of the contact area ratio, the greater the sweat absorbability effect and the more superior the feeling of comfort is. However, when the contact area with regard to the skin is excessively high in conventional known elastic materials, instead of improving the abovementioned effect, the sticky feeling remains, and thus, the comfort of the wearer cannot be maintained. Moreover, a reduced contact area, on the other hand, causes a plurality of spaces between the skin surface and the sheet, thus causing insufficient sweat absorbability. The composite sheet of the present invention allows for the abovementioned problem(s) to be solved and improves the comfort of the wearer when worn, by promoting the absorption, transmission, and the transpiration of sweat.

Figure 7A:
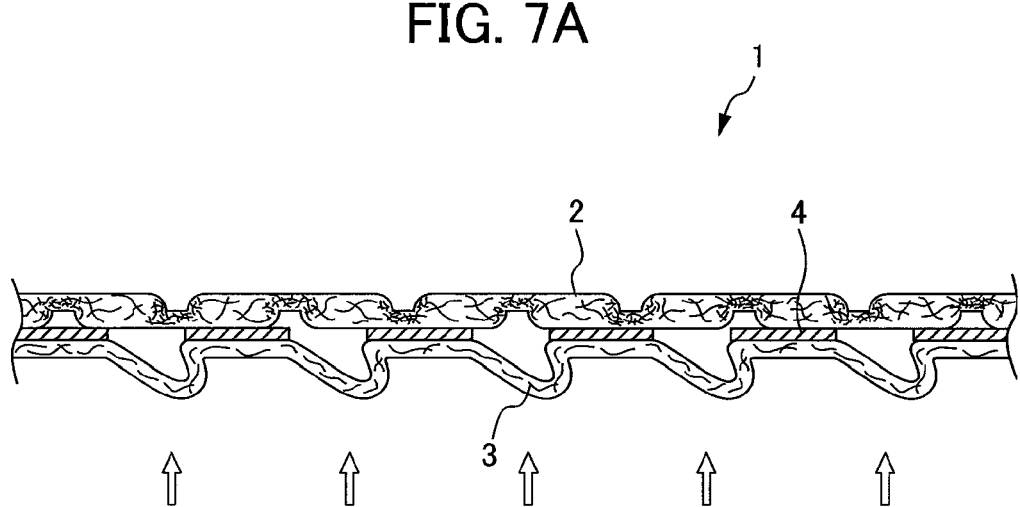
FIG. 7A is schematic view illustrating a surface of a non-elastic sheet of the composite sheet according to the present invention while in close contact with a skin surface.
Figure 7B:
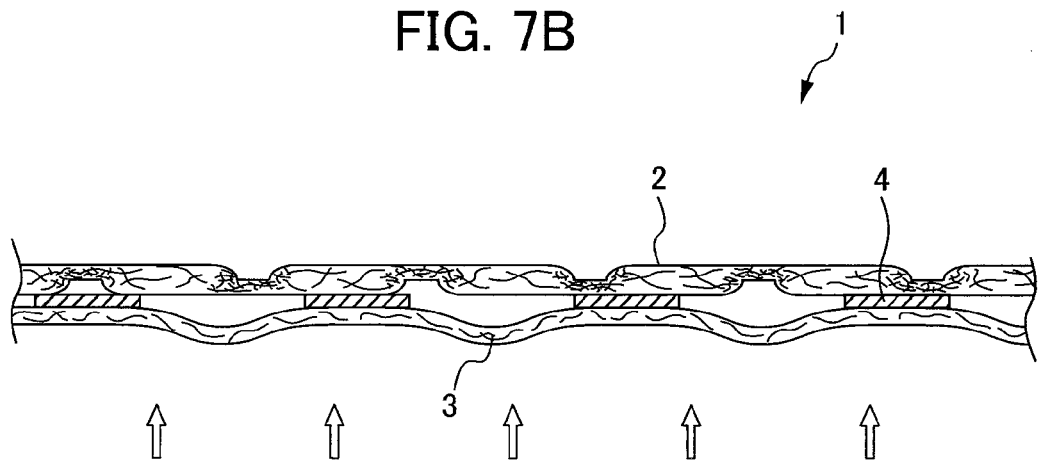
FIG. 7B is schematic view illustrating a surface of a non-elastic sheet of the composite sheet according to the present invention while in close contact with a skin surface.

FIGS. 7A and 7B illustrate a contact state when the non-elastic sheet 3 of the composite sheet 1 of FIG. 2 is abutted to the skin surface. FIG. 7A is a conceptual diagram illustrating the state at the time of 135% elongation in the manufacturing flow direction. FIG. 7B is a conceptual diagram illustrating the state at the time of 170% elongation in the manufacturing flow direction. In FIGS. 7A and 7B, the skin is abutted to the composite sheet 1 in direction indicated by the arrows. Moreover, the time of 135% elongation in the manufacturing flow direction (described hereinafter) is determined by assuming the elongation level of the wearer during normal wear of the diaper, in which the composite sheet 1 is used as a chassis of a disposable diaper. The time of 170% elongation in the manufacturing flow direction is determined by assuming the maximum elongation of the composite sheet.

In FIGS. 7A and 7B, when the non-elastic sheet 3 is abutted to skin surface, the unattached parts of the non-elastic sheet 3 sag to thereby cause a plurality of small wrinkles. The plurality of small wrinkles are supported by the adhesive agent 4 formed on the elastic nonwoven fabric 2 at equal interval. Accordingly, the plurality of small wrinkles are stably formed on the elastic nonwoven fabric 1. Moreover, since these wrinkles are formed only by the non-elastic sheet 3, the wrinkles easily deform at low stress. Accordingly, the contact area ratio can be increased.

Figure 8A:
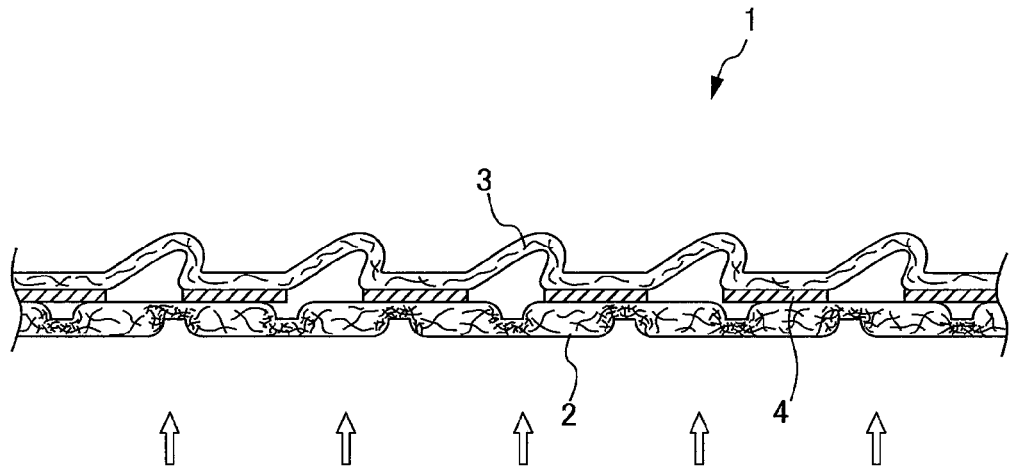
FIG. 8A is schematic view illustrating a surface of an elastic nonwoven fabric of the composite sheet according to the present invention while in close contact with the skin surface.
Figure 8B:
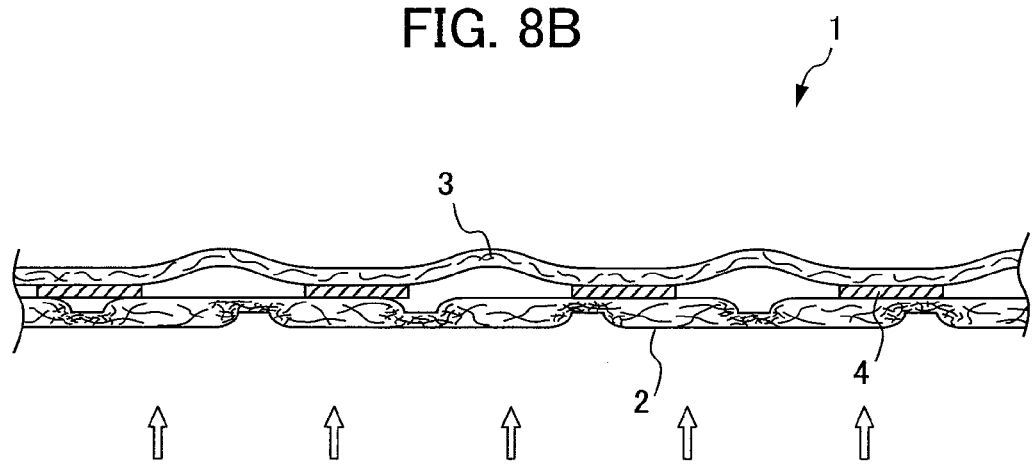
FIG. 8B is schematic view illustrating a surface of an elastic nonwoven fabric of the composite sheet according to the present invention while in close contact with the skin surface.

FIGS. 8A and 8B shows contact state when the elastic nonwoven fabric 2 of the composite sheet 1 of FIG. 2 is abutted with the skin surface. In this case, the smooth elastic nonwoven fabric 2 can provide a contact area ratio higher than that of FIGS. 7A and 7B.

Figure 9A:
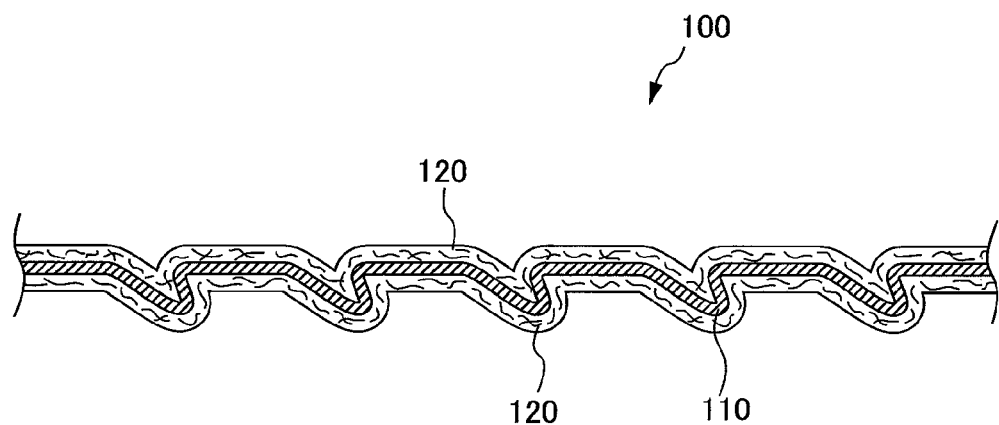
FIG. 9A is schematic view illustrating a conventional composite sheet while in close contact with the skin surface.
Figure 9B:
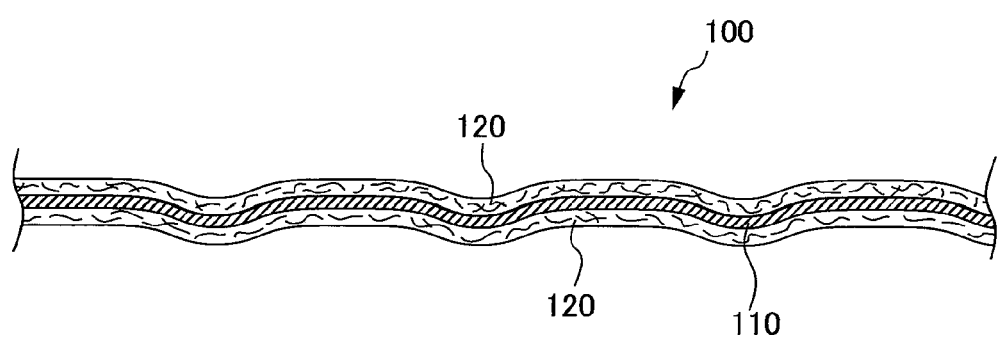
FIG. 9B is schematic view illustrating a conventional composite sheet while in close contact with the skin surface.

On the other hand, FIGS. 9A and 9B shows constituent member 100 employed in a waist gather section of a conventional disposable diaper. The constituent member 100 is structured such that the two non-elastic sheets 120 have a linear elastic member 110 therebetween. In this case, the linear elastic member 110 elongates to causes large wrinkles that are twisted and unstable. Moreover, since the wrinkles from are crushed due to the stress from being abutted to the skin of the wearer, the rigidity and thickness of the entire body thereof are increased. Accordingly, the contact area is reduced, leading to increased discomfort caused by inferior sweat absorbability.

Moreover, the contact area ratio in the present invention is a value measured by the below-mentioned method.

a) First, a composite sheet in a predetermined elongated state (the elongations of 135% and 170% both being in the manufacturing flow direction) is fixed onto a flat surface of a support plate, such that a measuring surface thereof faces upwards (a test fragment having a size of 50 mm×50 mm in the elongated state);

b) Next, the measuring surface of the composite sheet is evenly coated with a water-based paint (obtained by mixing paint with water at a ratio of 2:1; the paint being blue-colored "Sakura Mat Watercolor Watercolor Paint", manufactured by Sakura Color Products Corp.);

c) A No. 2 filter paper (50 mm×50 mm; manufactured by Toyo Koshi Co., Ltd.) is superimposed on the measuring surface, and retained thereon for 10 seconds under 250 g (including the flat plate) of weight; and d) The percentage of the area of the water-based paint transferred to the filter paper is calculated by the binarization via image analysis to obtain a contact area ratio (%).

Airflow Resistance Value

When the abovementioned contact area ratio is at least 65%, sweat is absorbed favorably. However, in order to ensure comfort while the diaper is being worn by the wearer, the composite sheet must also have a breathability of at least a predetermined value. Accordingly, the composite sheet of present invention is one in which the airflow resistance value of no greater than 0.20 KPa·s/m at the time of 150% elongation in the manufacturing flow direction. If the airflow resistance value is within this range, since the transpiration of absorbed sweat is superior, the comfort of the wearer is not adversely effected.

Moreover, the "airflow resistance value" of the present invention, which is one index of the breathability, can be measured by a KES-F8 measuring instrument manufactured by Kato Tech Co., Ltd., for example. Furthermore, the airflow resistance values obtained by this measurement method, which are within a range 0.06 KPa·s/m to 1.245 KPa·s/m, correlate with the converted values from Frazier-type air permeability flow rates.

Condensation Amount

The composite sheet of the present invention preferably has a condensation amount of no greater than 7 $g/m^2$ at the time of 150% elongation in the manufacturing flow direction. This condensation amount is a parameter that also dependent on the abovementioned contact area ratio. In cases where the condensation amount greater than 7 $g/m^2$, sweat absorption becomes insufficient, thus reducing the comfort of the wearer.

Moreover, the condensation amount in the present invention is a value measured by the following method:

a) 400 cc of water having a temperature of 40 degrees C. is poured into a 500 cc beaker;

b) The composite sheets in a predetermined elongated position (opposing distance of 20 mm) are arranged to oppose each other, such that the measuring surfaces are facing (that have a distance of 20 mm between the opposing composite sheets), and left under an atmosphere of 20 degrees C.×60% RH for one hour; and c) The amount of water collected via this measuring surface is absorbed by the filter paper, and the amount of condensation ($g/m^2$) is determined by converting the amount water absorption per unit area (the weight difference of the filter paper before and after water absorption).

Transpiration Rate

The composite sheet of the present invention preferably has a transpiration rate of at least 65% at the time of 150% elongation in the manufacturing flow direction. This transpiration amount is a parameter which dependent on the abovementioned breathability. The transpiration rate is preferably at least 65%, more preferably at least 70%, even more preferably at least 75%, and most preferably at least 80%. The transpiration amount of at least 65% allows for quick transpiration of absorbed sweat to be provided, and thus, maintain the comfort of the wearer. Moreover, the transpiration rate preferably has an upper limit of no greater than 99%.

Furthermore, the transpiration rate of the present invention is a value measured by the following method:

a) The temperature of artificial skin (manufactured by Idemitsu Technofine Co., Ltd.; PBZ13001) is adjusted to 36 degrees C.;

b) A sprayer is used to 1.0 g of water in the form of a spray onto a 70 mm×70 mm region of the surface of the artificial skin;

c) The measuring surface of the composite sheet is mounted to face the artificial skin side, left under a 196 g/70 mm×70 mm weight under the atmosphere of 20 degrees C.×60% RH (absorption), and subsequently, the weight removed;

d) Afterwards, the composite sheet was further left under the atmosphere of 20 degrees C.×60% RH for an additional 20 minutes (transpiration); and e) 1.0 g−(minus) the amount of water remaining on the artificial skin−(minus) the amount of water adhered to the measuring surface=the transpiration amount (g), and the transpiration rate determined as the percentage (%) of the transpiration amount with respect to the amount of the water sprayed.

Moisture Permeation Level

The composite sheet of the present invention preferably has a moisture permeation level of at least 3000 $g/m^2$·24 hours·atom at the time of 150% elongation in the lateral direction. When the moisture permeation level is within this range, rapid transpiration of absorbed sweat can be provided, and thus, the comfort of the wearer maintained.

Moreover, the moisture permeation level of the present invention is a value obtained by a ASTM E 96 to 66 deformation method, or JISZ0208 deformation method (the cup method), and is the measurement value of water in a cup under the atmosphere of 40 degrees C.×60% RH.

[Absorbent Article]

The above composite sheet 1 can be used for a disposable diaper that is an absorbent article, for example. Moreover, the side opposing the body of the wearer is a skin-abutting surface side, and the side opposing the skin-abutting surface is a nonskin-abutting surface side.

Figure 10:
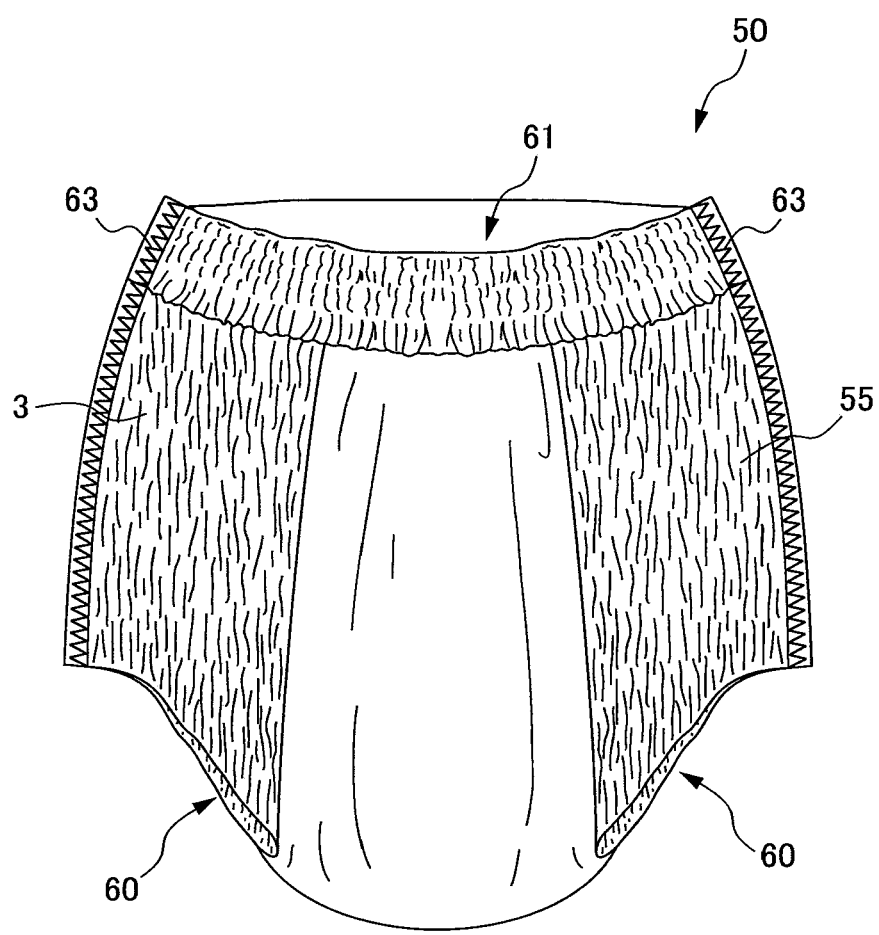
FIG. 10 is a front view illustrating a disposable diaper as one example of an absorbent article employing the composite sheet according to the present invention.

FIG. 10 is a front view illustrating a pants-type disposable diaper 50 that as one example of the absorbent article employing the composite sheet of the present invention. FIG. 11 is a development view illustrating the disposable diaper 50. The disposable diaper 50 includes: a chassis 54 constituting the main body; a liquid-permeable surface sheet 51 provided at the skin-abutting surface of the chassis 54; a non-liquid-permeable back face sheet 53 provided at the no-skin-abutting surface side of the chassis 54; and a liquid-retaining absorber core 52 disposed between the surface sheet 51 and the chassis 54.

The chassis 54 includes: a front side 55, and a rear side 56 forming a pants-type diaper. The chassis 54 has a front waist gather 57 forming an end of the front side 55, and a rear waist gather 58 forming an end of the rear side 56. At both edges in the longitudinal direction of the chassis 54, substantially U-shaped notches 59 are formed to have a vertex at substantially the center in the width direction. The notches 59 constitute leg openings 60 when the front side 55 and the rear side 56 of the chassis 54 are bonded by bonded sections 63 to constitute a pants-type diaper. The front side 55 is bonded to the rear side 56 to form a waist opening 61.

In this embodiment, the stretchable composite sheet 1 is used as the chassis 54, and is arranged so that the elongation direction is the width direction WD in FIG. 11. Thus, the waist gathers 57 and 58 do not include an elastic member such as a rubber thread. When the front side 55 and the rear side 56 of the chassis 54 are bonded to form a pants-type diaper, the composite sheet 1 allows the front side 55 and the rear side 56 to be elongated along the outer periphery of the pants. Accordingly, the disposable diaper 50 is elongated in accordance with the movement of the wearer when the wearer wears the diaper, or when the wearer wearing the diaper moves. The elimination of an elastic member described above can reduces the physical irritation to the skin. However, the present invention may also employ an elastic member, when needed, for a waist gather or a leg gather.

Moreover, the composite sheet 1 of this embodiment is arranged so that an elastic nonwoven fabric 2 functions as the skin-abutting surface shown in FIGS. 8A and 8B. Thus, wrinkles, due to the non-elastic sheet 3, appear at the surface, as illustrated in FIG. 10. However, the present invention is not specifically limited to the abovementioned arrangement. For example, the non-elastic sheet 3 of composite sheet 1 may also function as the skin surface. However, the abovementioned arrangement of this embodiment is more preferable, due to a higher contact area ratio to the skin.

Moreover, although the present embodiment describes a pants-type disposable diaper, the present invention is not specifically limited to such an embodiment. The composite sheet of the present invention may also be used for other products. For example, the composite sheet may be used as a side flap of tape-type absorbent article, a side stretch sheet of side stretch-type and pants-type diaper, wings of a napkin for fixing the napkin to undergarments, an elastic member of cuffs, etc., of a disposable scrub gown, an ear band of a disposable mask, a disposable bandage, or a surface material of a fomentation material, for example.

EXAMPLES

The following section will describe illustrative embodiments of the present invention. These illustrative embodiment are mere illustration for favorably describing the present invention and do not limit the present invention.

Example 1

The raw elastic nonwoven fabric 5 was prepared by mixing polypropylene fibers (PP) with polyurethane fibers (TPU) at a ratio of 45:55. Next, the elastic nonwoven fabric original fabric 5 was subjected to the gear elongation processing via filler roll 10 in the manufacturing flow direction, to thereby obtain the elastic nonwoven fabric 2. The raw elastic nonwoven fabric 5 had a basis weight of 35 g/m$^2$.

Then, the elastic nonwoven fabric 2 was elongated in the manufacturing flow direction to be 2.3 times larger than normal size, and hot-melt adhered to a non-elastic sheet 3 having a basis weight of 19 g/m$^2$ (polypropylene spunlaid nonwoven fabric), to thereby obtain the composite sheet 1. Moreover, the adhesive agent 4 was coated onto the non-elastic sheet 3 to form a coating pattern via spiral coating and the hot-melt adhesive agent having a basis weight of 2 g/m$^2$. The resultant composite sheet 1 showed a maximum elongation rate of 210% and a thickness of 1.8 mm.

COMPARATIVE EXAMPLES

The composite sheet having the below-mentioned structure was used as a constituent member of a commercially-available disposable diaper employed in Comparative Example 1 and Comparative Example 2.

Comparative Example 1

Polypropylene spunbond nonwoven fabric (basis weight of 19 g/m$^2$)/elastic member (elastic thread)/polypropylene SMS nonwoven fabric (basis weight of 15 g/m$^2$)/polypropylene spunbond nonwoven fabric (basis weight of 19 g/m$^2$).

Comparative Example 2

Polypropylene point bond nonwoven fabric (basis weight of 28 g/m$^2$)/elastic member (mesh film, basis weight of 70 g/m$^2$)/polypropylene point bond nonwoven fabric (basis weight of 28/m$^2$)

Experimental Example 1

With regard to Example 1a, Example 1b, Comparative Example 1, and Comparative Example 2, the abovementioned measurement method was employed to measure a contact area ratio, an airflow resistance value, a condensation amount, a transpiration rate, and a moisture permeation level. The results thereof are shown in Table 1.

Furthermore, when the composite sheet of Example 1a is employed in a disposable diaper, the elastic nonwoven fabric-side is the skin-abutting surface. The contact area ratio, the condensation amount, the transpiration rate, and the moisture permeation level were measured based on the assumption that the elastic nonwoven fabric-side is the measuring surface. The airflow resistance value was obtained by measuring the airflow resistance from the elastic nonwoven fabric-side. When the composite sheet of Example 1b is employed in a disposable diaper, the non-elastic sheet-side is assumed to be the skin-abutting surface. The contact area ratio, the condensation amount, the transpiration rate, and the moisture permeation level were measured by assuming that the non-elastic sheet-side is the measuring surface. The airflow resistance value was obtained by measuring the airflow resistance from the elastic nonwoven fabric-side.

TABLE 1

|  |  | EXAMPLE 1a | EXAMPLE 1b | COMPARATIVE EXAMPLE 1 | EXAMPLE 2 |
|---|---|---|---|---|---|
| CONTACT AREA RATIO (%) | 135% ELONGATION | 92.7 | 81.0 | 58.2 | 65.4 |
|  | 170% ELONGATION | 95.5 | 68.5 | 59.3 | 53.3 |
| AIRFLOW RESISTANCE VALUE (KPa·s/m) |  | 0.034 | 0.034 | 0.100 | 0.536 |
| CONDENSATION AMOUNT (g/m$^2$) |  | 0.015 | 0.034 | 0.066 | 0.329 |
| TRANSPIRATION RATE (%) |  | 84 | 77 | 60 | 56 |
| MOISTURE PERMEATION LEVEL (g/m$^2$ · 24 hour · atom) |  | 3551 | 3746 | 3544 | 1829 |

As clearly indicated by the results of Table 1, in Examples 1a and 1b, the contact area ratio at either the time of 135% elongation in the manufacturing flow direction or at the time 170% elongation in the manufacturing flow direction was at least increased to 65%, and the airflow resistance value thereof was at least 0.20 KPa·s/m, thus demonstrating the superior sweat absorbability and breathability. In contrast, the elastic member employed in Comparative Example 1 exhibited a low contact area ratio of at least 60%, as well as a low transpiration rate of 60%. Moreover, a film-shaped elastomer is provided between the layers in Comparative Example 2, exhibited a high airflow resistance and a low transpiration rate, thereby leading to insufficient comfort.

The invention claimed is:

1. A composite sheet comprising an elastic nonwoven fabric in an elongated state bonded to a non-elastic sheet,
    wherein at least one surface of the composite sheet has a contact area ratio of at least 65% at a time of 135% elongation and at a time of 170% elongation, and
    the composite sheet has an airflow resistance value of no greater than 0.20 KPa·s/m at a time of 150% elongation, and
    wherein the contact area ratio is an area percentage of a water-based paint transferred to a filter paper after being applied onto one surface of the composite sheet in the elongated state, with the filter paper superimposing the water-based paint being retained thereon for 10 seconds under 250 g of weight, and
    wherein the elastic nonwoven fabric has a plurality of strip-shaped low-density regions and a plurality of strip-shaped high-density regions formed therein and are alternately and continuously formed on both sides thereof, with the strip-shaped high-density regions on one surface and the strip-shaped high-density regions on the other surface being alternately formed.

2. The composite sheet according to claim 1,
    wherein the non-elastic sheet is bonded to the elastic nonwoven fabric via an adhesive agent.

3. The composite sheet according to claim 1,
    wherein the composite sheet has a condensation amount of at least 7 g/m$^2$ at the time of 150% elongation, and
    wherein the condensation amount is the amount of water adhering to an opposing surface of the composite sheet after the composite sheet is arranged to oppose a water surface at a temperature of 40° C., and left for one hour under an atmosphere of 20° C.×60% RH.

4. The composition sheet according to claim 1,
    wherein the composite sheet has a transpiration rate of at least 65% at the time of 150% elongation.

5. The composition sheet according to claim 1,
    wherein the composite sheet has a moisture permeation level of at least 3000 g/m$^2$·24 hours·atom at the time of 150% elongation.

6. An absorbent article comprising at least an absorber and the composite sheet according to claim 1,
    wherein the composite sheet is mounted on a skin-abutting surface of the absorbent article when worn by a wearer.

7. The composite sheet according to claim 1, wherein each of the plurality of strip-shaped high-density regions is configured to be concave in a thickness direction of the elastic nonwoven fabric.

8. The composite sheet according to claim 1, wherein the plurality of strip-shaped high-density regions located on the one surface and the plurality of strip-shaped high-density regions located on the other surface of the elastic nonwoven fabric are configured to be geometrically offset with each other.

* * * * *

UNITED STATES PATENT AND TRADEMARK OFFICE
CERTIFICATE OF CORRECTION

PATENT NO. : 8,551,608 B2
APPLICATION NO. : 12/593425
DATED : October 8, 2013
INVENTOR(S) : Kawakami et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 853 days.

Signed and Sealed this
Fifteenth Day of September, 2015

Michelle K. Lee
*Director of the United States Patent and Trademark Office*